(12) United States Patent
Guan et al.

(10) Patent No.: US 11,497,448 B2
(45) Date of Patent: Nov. 15, 2022

(54) DEEP INTRACRANIAL ELECTRODE

(71) Applicant: NEUROECHOS MEDICAL (SHENZHEN) CO., LTD, Shenzhen (CN)

(72) Inventors: Xijun Guan, Shenzhen (CN); Xiaolong Mo, Shenzhen (CN)

(73) Assignee: NEUROECHOS MEDICAL (SHENZHEN) CO., LTD, Shenzhen (CN)

(*) Notice: Subject to any disclaimer, the term of this patent is extended or adjusted under 35 U.S.C. 154(b) by 605 days.

(21) Appl. No.: 16/549,624

(22) Filed: Aug. 23, 2019

(65) Prior Publication Data
US 2021/0015429 A1   Jan. 21, 2021

Related U.S. Application Data

(63) Continuation of application No. PCT/JP2019/096391, filed on Jul. 17, 2019.

(51) Int. Cl.
| | | |
|---|---|---|
| *A61B 5/00* | (2006.01) | |
| *A61B 5/24* | (2021.01) | |
| *A61B 5/291* | (2021.01) | |

(52) U.S. Cl.
CPC ............ *A61B 5/6868* (2013.01); *A61B 5/24* (2021.01); *A61B 5/291* (2021.01); *A61B 5/4094* (2013.01); *A61B 2562/16* (2013.01)

(58) Field of Classification Search
CPC ......... A61B 5/24; A61B 5/2415; A61B 5/283; A61B 5/287; A61B 5/291; A61B 5/293; A61B 5/6847; A61B 5/6868
See application file for complete search history.

(56) References Cited

U.S. PATENT DOCUMENTS

| | | | | |
|---|---|---|---|---|
| 8,244,346 | B2* | 8/2012 | Foster | A61N 1/056 607/116 |
| 8,968,331 | B1* | 3/2015 | Sochor | A61B 17/3468 606/129 |
| 2007/0088210 | A1* | 4/2007 | Woo | G01R 33/4808 600/410 |
| 2010/0317921 | A1* | 12/2010 | Marple | A61B 5/6853 600/116 |
| 2012/0253340 | A1* | 10/2012 | Stevenson | H03H 7/0123 607/116 |
| 2018/0116645 | A1* | 5/2018 | Nosler | A61B 10/0283 |

FOREIGN PATENT DOCUMENTS

| | | | |
|---|---|---|---|
| CN | 104083823 A | * 10/2014 | |
| WO | WO-2013056243 A1 | * 4/2013 | ......... A61B 17/3401 |

* cited by examiner

*Primary Examiner* — Eun Hwa Kim
(74) *Attorney, Agent, or Firm* — Hamre, Schumann, Mueller & Larson, P.C.

(57) ABSTRACT

A deep intracranial electrode which comprises a conducting wires, an electrode contact, a connector and a nonelastic sleeve is provided, one end of the conducting wires connected to the electrode contact, the other end connected to the connector; the nonelastic sleeve sheathes around the conducting wires, and one end of the nonelastic sleeve is capable of being connected to the connector, the other end connected to the fixing nut which is fixed to a skull. When the deep intracranial electrode is under a pulling force, the fixing nut may avoid the nonelastic sleeve from moving, thereby avoiding the deep intracranial electrode from being pulled out.

15 Claims, 7 Drawing Sheets

DEEP INTRACRANIAL ELECTRODE

CROSS-REFERENCE TO RELATED APPLICATION

This application is a continuation of PCT application No. PCT/CN2019/096391, filed on Jul. 17, 2019. The patent application is hereby incorporated by reference in its entirety.

TECHNICAL FIELD

The present disclosure relates to the field of medical apparatuses and equipment, more particularly, to a deep intracranial electrode.

BACKGROUND

Prior to performing operation to a patient with intractable epilepsy, a deep intracranial electrode is required to monitor intracranial electroencephalograph so as to determine the location of the intractable epilepsy. The deep intracranial electrode normally includes an electrode contact and a connector. The electrode contact is electrically connected to the connector. One end of the deep intracranial electrode arranged with the electrode contact may be implanted surgically into the skull of the patient. The connector may be connected to the electroencephalograph, such that electrophysiological signals collected by the electrode contact may be transmitted to the electroencephalograph.

Prior to detection, the skull of the patient needs to be perforated, and then a guidance screw is screwed to the skull of the patient. The guidance screw is connected in thread to a fixing nut. The fixing nut may limit motion of the guidance screw relative to the skull of the patient. The end of the deep intracranial electrode arranged with the electrode contact passes through the guidance thread and deep into the skull of the patient. However, in the process of electroencephalography detection, the deep intracranial electrode may be pulled out accidentally, interrupting the detection.

SUMMARY

The present disclosure desires to provide a deep intracranial electrode, and aims to deal with the issue that in the process of electroencephalography detection, the deep intracranial electrode may be pulled out accidentally, interrupting the detection.

In order to solve the issue above, the present disclosure provides a deep intracranial electrode which comprises conducting wires, electrode contacts, a connector and a nonelastic sleeve. One end of each conducting wire is connected to the electrode contact, the other end is connected to the connector; the nonelastic sleeve sheathes around the conducting wires, and one end of the nonelastic sleeve is capable of being connected to the connector, the other end is connected to the fixing nut which is fixed to a skull.

Optionally, a part of the conducting wires contained within the nonelastic sleeve is longer than the nonelastic sleeve.

Optionally, the nonelastic sleeve is made of a transparent material.

Optionally, one end of the nonelastic sleeve sheathes around the connector, the other end sheathing around the fixing nut.

Optionally, the nonelastic sleeve is made of a non-magnetic material.

Optionally, the deep intracranial electrode further includes a connecting member, one end of the connecting member is connected to the electrode contact, the other end connected to the connector; and a part of the connecting member between the electrode contact and the connector is shorter than a part of the conducting wires between the electrode contact and the connector.

Optionally, the connecting member is made of a tensile material.

Optionally, the deep intracranial electrode further includes a shield sleeve that sheathes around the conducting wires, the shield sleeve being shorter than the conducting wires, and the conducting wires are capable of being folded inside the shield sleeve.

Optionally, the deep intracranial electrode further includes a shield sleeve that sheathes around the conducting wires, the shield sleeve being capable of moving axially along and relative to the conducting wires so as to change a length of a part of the shield sleeve sheathing around the conducting wires.

Optionally, the connector comprises a casing and pins arranged inside the casing, the casing connected to the connecting member; a plurality of conducting wires, pins and electrode contacts are arranged, each conducting wires connected to each pin and each electrode contact.

Optionally, the conducting wires and the electrode contacts are both made of non-magnetic materials.

Optionally, the deep intracranial electrode further includes a flexible insulation sleeve sheathing around the conducting wires. One end of the flexible insulation sleeve connected to the electrode contact, the other end connected to the connector; the deep intracranial electrode further includes a rigid support rod, the rigid support rod passing through the flexible insulation sleeve and located at one end of the flexible insulation sleeve connected to the electrode contact.

Optionally, the rigid support rod is made of a shape memory material.

Optionally, the deep intracranial electrode further includes an end electrode, the end electrode connected to one end of the rigid support rod away from the connecting member and electrically connected to the connector via the wire.

Optionally, each of the electrode contacts is of an annular shape.

Beneficial effects of embodiments of the present disclosure include:

In the deep intracranial electrode above, by arranging the nonelastic sleeve sheathing around the conducting wires, one end of the nonelastic sleeve is connected to the connector, the other end is connected to the fixing nut that is fixed to the skull. When the deep intracranial electrode is under a pulling force, the fixing nut may avoid the nonelastic sleeve from moving, thereby avoiding the deep intracranial electrode from being pulled out.

BRIEF DESCRIPTION OF THE ACCOMPANYING DRAWINGS

In order to describe the embodiments of the present disclosure and the prior art more clearly, the drawings required for describing the embodiments of the present disclosure and the prior art are briefly introduced. Apparently, the drawings below merely represent some embodiments of the present application. For those ordinarily skilled in the field, alternative drawings may be obtained without pay creative works.

Reference numbers in the description are as follows:
100. deep intracranial electrode;
10. conducting wires;
20. electrode contact;
30. connector;
40. shield sleeve;
50. rigid support rod;
60. end electrode;
70. nonelastic sleeve;
80. flexible insulation sleeve;
200. fixing nut.

DETAILED DESCRIPTION OF ILLUSTRATED EMBODIMENTS

Technical solutions in the embodiments of the present disclosure will be described below clearly and completely with reference to the drawings. Obviously, the embodiments described herein are only some, but no exclusive embodiments of the present disclosure. Based on the embodiments described in this present disclosure, all other embodiments obtained by those ordinarily skilled in the field without paying creative works should fall within the scope of the present application.

One embodiment of the present application provides a deep intracranial electrode 100 to detect electrophysiological activities in deep brain tissue of a patient. The deep intracranial electrode 100 comprises conducting wires 10, an electrode contact 20 and a connector 30. One end of each conducting wire 10 is connected to the electrode contact 20, the other end is connected to the connector 30.

In the embodiment, the connector 30 comprises a casing and pins arranged inside the casing. A plurality of conducting wires 10, pins and electrode contacts 20 are arranged in plural, each conducting wires 10 connected to each pin and each electrode contact 20. Each of the pins inside the connector 30 is independent from each other with high integration level, which is convenient for connection to an electroencephalograph.

Figure 1:
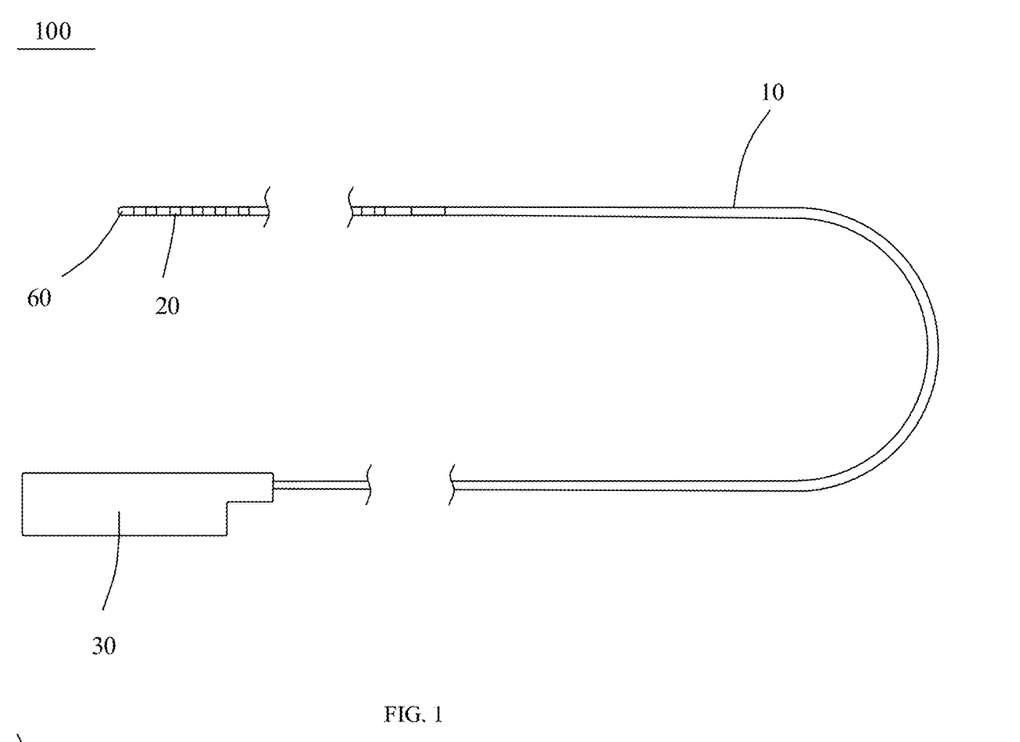
FIG. 1 is a schematic view of a partial structure of a deep intracranial electrode according to an embodiment of the present application.
Figure 2:
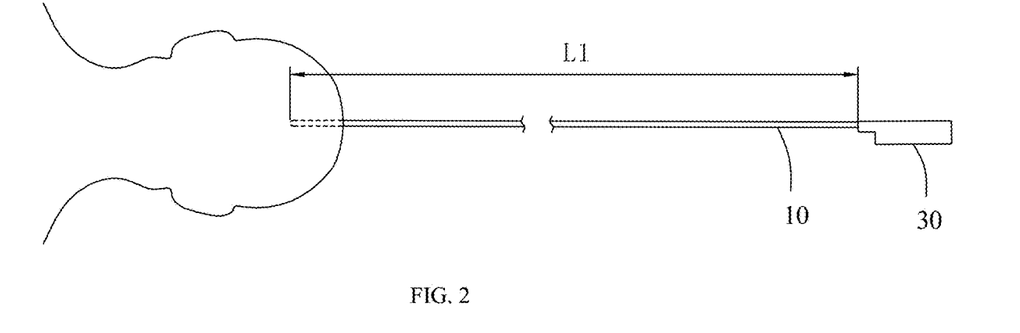
FIG. 2 is a schematic view of an original state of a conducting wire when the deep intracranial electrode in FIG. 1 is implanted into the skull of a patient.
Figure 3:
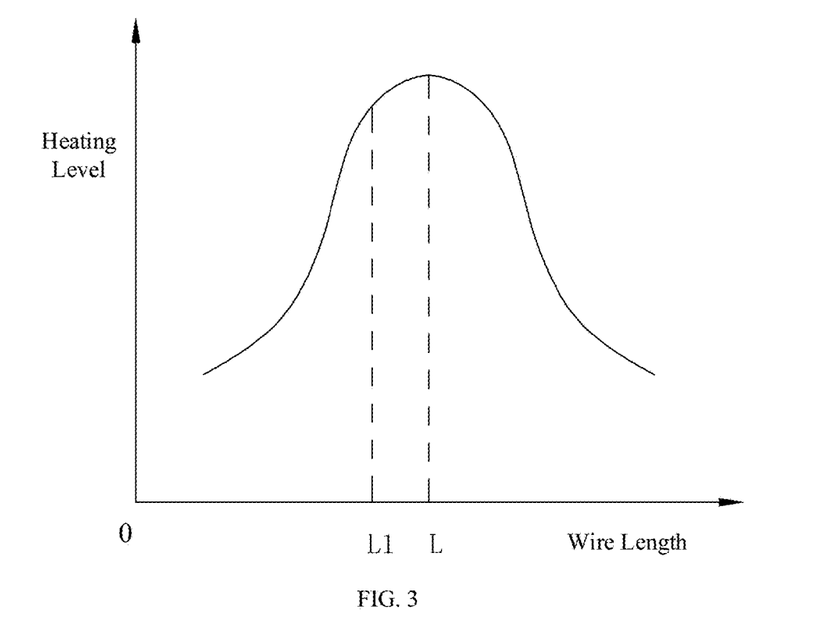
FIG. 3 is a relation graph of a heating level of the conducting wires of the deep intracranial electrode in FIG. 2 versus a length of the conducting wires.

As shown in FIG. 2, one end of the deep intracranial electrode 100 arranged with the electrode contact 20 is capable of being implanted into the skull of the patient, such that the electrode contact 20 may collect electrophysiological signals in deep brain tissue of the patient. Since the conducting wires 10 is of a slender structure, it may absorb radio-frequency magnetic field energy generated by a magnetic resonance equipment, and produce energy deposition at an end of the conducting wires 10, which results in heating of the electrode contact 20 connected to the conducting wires 10. As shown in FIG. 3, the heating level of the conducting wires 10 of the deep intracranial electrode 100 varies along with the length of the conducting wires 10 with a peak value. The length of the conducting wires 10 corresponding to the peak value is a resonance length of the conducting wires 10. For illustrative purpose, the resonance length of the conducting wires 10 is called L. As shown in FIG. 3, the further away the length of the conducting wires 10 is from the resonance length L of the conducting wires 10, the lower the heating level of the conducting wires 10 is.

Figure 4:
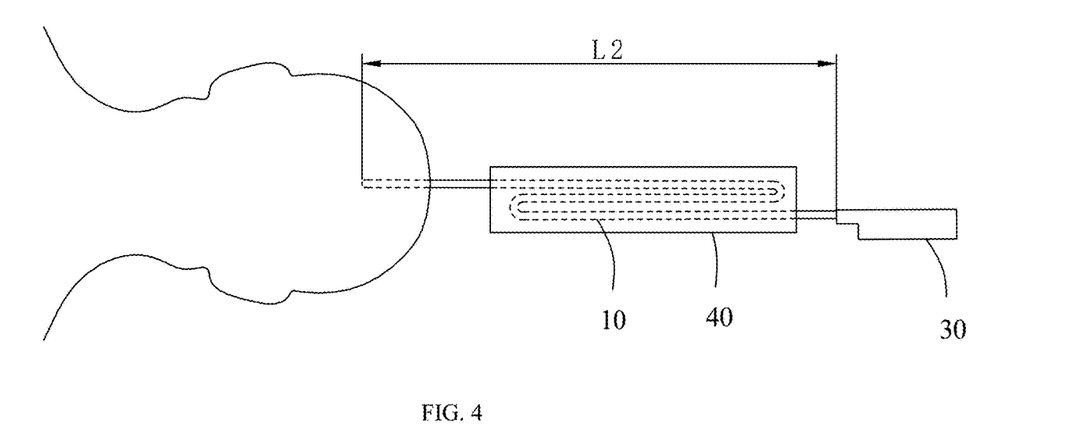
FIG. 4 is a schematic view of the deep intracranial electrode in FIG. 2 with the length of the conducting wires adjusted.
Figure 5:
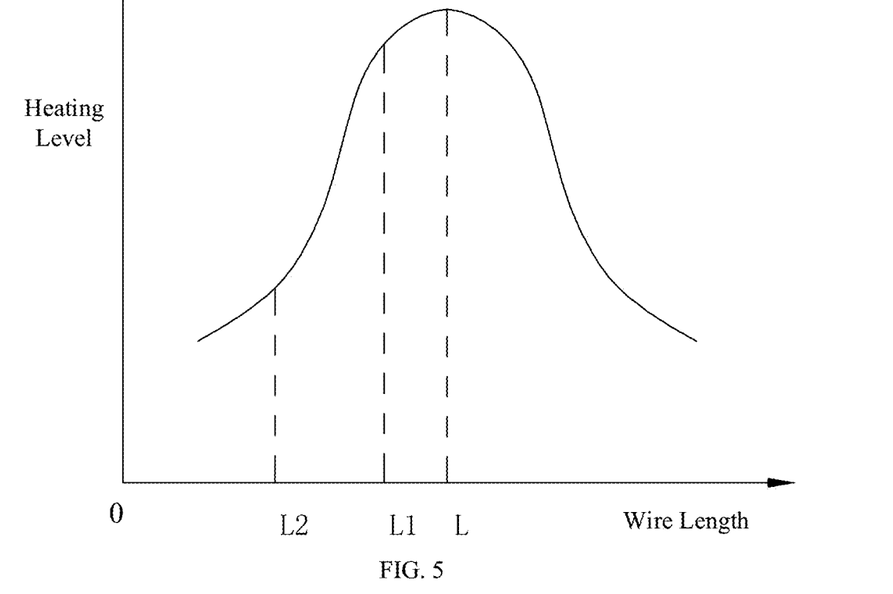
FIG. 5 is a relation graph of a heating level of the conducting wires of the deep intracranial electrode in FIG. 4 versus a length of the conducting wires.

As shown in FIG. 4, in order to lower heating level of the conducting wires 10. The deep intracranial electrode 100 in the present application further includes a shield sleeve 40. The shield sleeve 40 may sheath around the conducting wires 10, and the shield sleeve 40 is shorter than the conducting wires 10. Partial structure of the conducting wires 10 is folded inside the shield sleeve 40. By arranging the shield sleeve 40 shielding radio-frequency electromagnetic wave generated by a magnetic resonance equipment, the length of the conducting wires 10 inside the radio-frequency magnetic field of the magnetic resonance equipment may equal to a sum of the length of the shield sleeve 40 and a length of the conducting wires 10 outside the shield sleeve 40. For illustrative purpose, the actual length of the conducting wires 10 is called L1, the equivalent length of the conducting wires 10 is called L2. As shown in FIG. 5, the equivalent length L2 of the conducting wires 10 is lower than the actual length L1 of the conducting wires 10, and L2 is further away from the resonance length that L1 is. Therefore, the heating level of the end of the conducting wires 10 is reduced, improving safety performance of the deep intracranial electrode 100. In order to avoid the shield sleeve 40, which sheaths around the conducting wires 10, from moving relative to the conducting wires 10, the shield sleeve 40 may be fasten to the conducting wires 10 with a ribbon or a hoop. Surely, the shield sleeve 40 may be avoided from move randomly by controlling an inner diameter of the shield sleeve 40.

Figure 6:
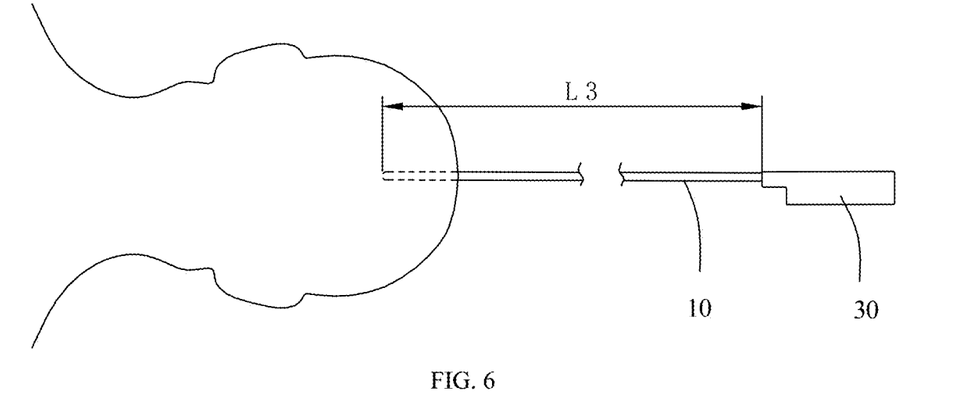
FIG. 6 is a schematic view of an original state of conducting wires of a deep intracranial electrode with another length implanted into the skull of the patient.
Figure 7:
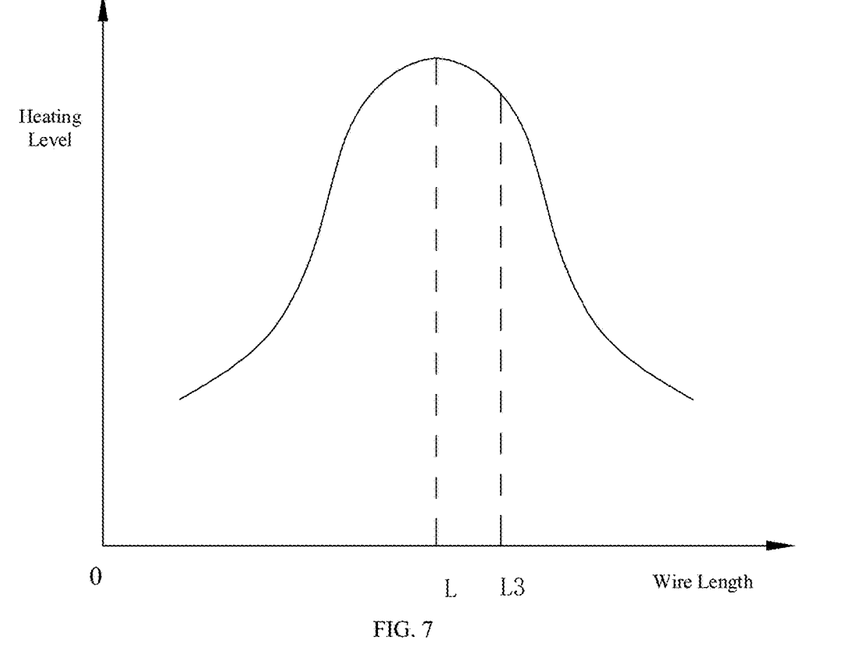
FIG. 7 is a relation graph of a heating level of the conducting wires of the deep intracranial electrode in FIG. 6 versus a length of the conducting wires.
Figure 8:
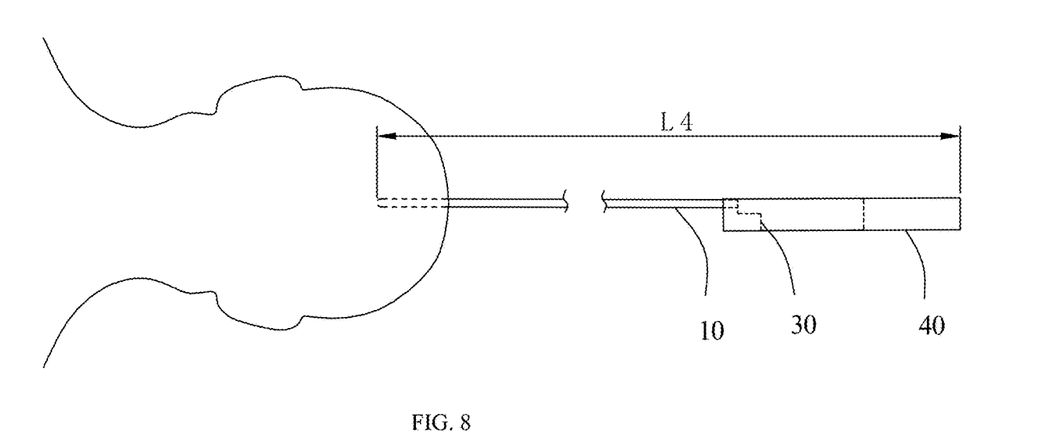
FIG. 8 is another schematic view of the deep intracranial electrode in FIG. 6 with the length of the conducting wires adjusted.
Figure 9:
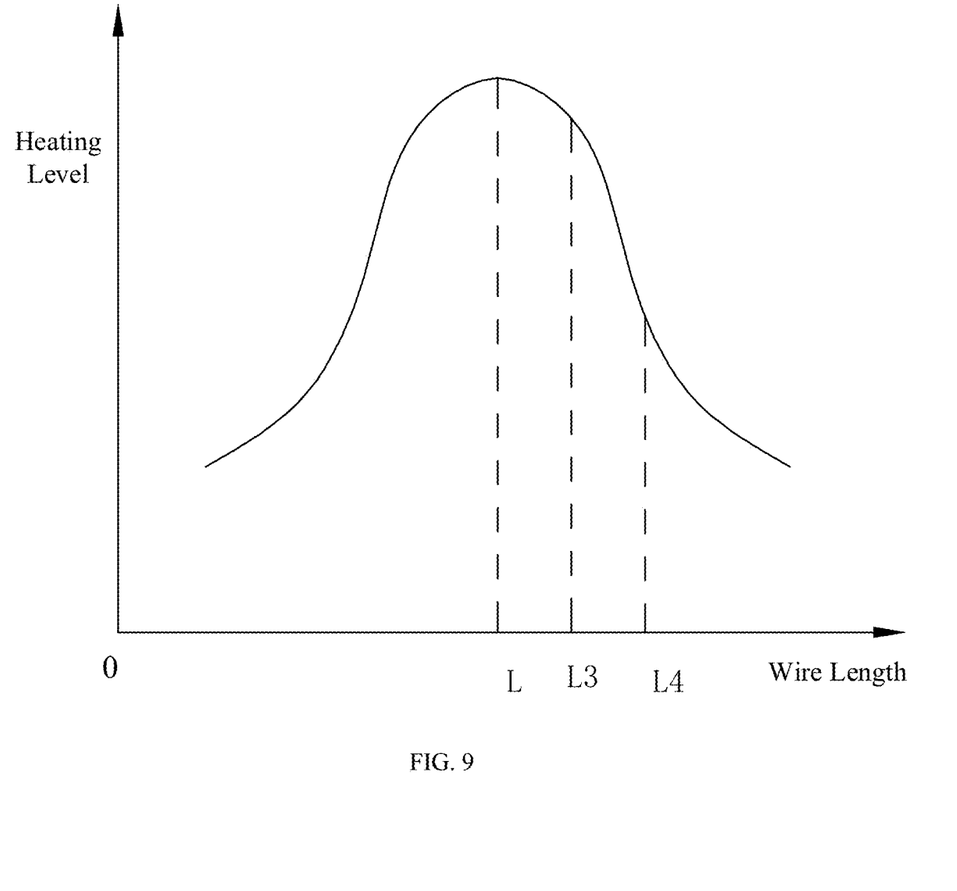
FIG. 9 is a relation graph of a heating level of the conducting wires of the deep intracranial electrode in FIG. 8 versus a length of the conducting wires.

As shown in FIG. 6 and FIG. 7, in another embodiment, the actual length of the conducting wires 10 is greater than the resonance length L of the conducting wires 10. In order to lower heating level of the conducting wires 10, the shield sleeve 40 sheaths around the conducting wires 10, such that the equivalent length of the conducting wires 10 is greater than the actual length L of the conducting wires 10. For illustrative purpose, the actual length of the conducting wires 10 is called L3, the equivalent length of the conducting wires 10 is called L4. As shown in FIG. 8, the shield sleeve 40 may move axially along and relative to the conducting wires 10 so as to change the length of a part of the shield sleeve 40 sheathing around the conducting wires 10. As shown in FIG. 9, the equivalent length L4 of the conducting wires 10 is greater than the actual length L3 of the conducting wires 10, and L4 is further away from the resonance length that L3 is. Therefore, the heating of the end of the conducting wires 10 is reduced, improving safety performance of the deep intracranial electrode 100.

It is to be understood that the resonance length L of the conducting wires 10 is relevant to parameters of the magnetic resonance equipment. For an identical conducting wires 10, resonance length L varies with different magnetic resonance equipment. The length of the conducting wires 10 located inside the shield sleeve 40 can be adjusted according to user's actual need, such that the equivalent length of the conducting wires 10 is further away from the resonance length L of the conducting wires 10 than the actual length of the conducting wires 10 is, lowering heating risk of the end of the conducting wires 10. Furthermore, the user may choose shield sleeves 40 with different lengths, so as to change the sum of the length of the shield sleeve 40 and a length of the conducting wires 10 arranged outside the shield sleeve 40.

It's worth mentioning that in the present embodiment, the conducting wires 10, the electrode contacts 20 and the pins are all made of non-magnetic materials, such as non-magnetic metal materials, conductive polymer materials, carbon nano-tubes or graphene materials. The non-magnetic materials may avoid the conducting wires 10, the electrode contacts 20 and the pins from interfering magnetic field environment of the magnetic resonance equipment, so as to avoid the magnetic resonance equipment from generating artifacts.

Figure 10:
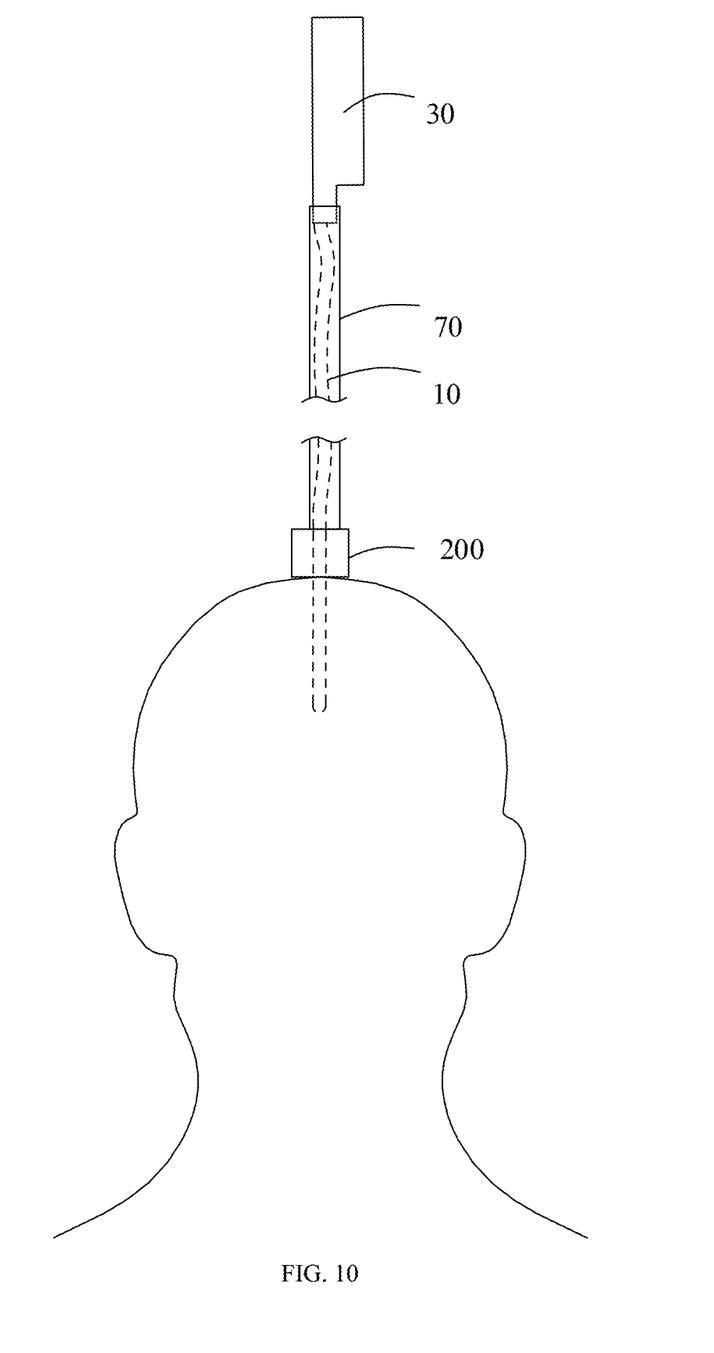
FIG. 10 is a schematic view of the deep intracranial electrode in FIG. 1 implanted into the skull of the patient.

Furthermore, in the present embodiment, as shown in FIG. 10, the deep intracranial electrode 100 further includes a nonelastic sleeve 70 which may sheath around the conducting wires 10. One end of the nonelastic sleeve 70 is connected to the connector 30, the other end connected to the fixing nut 200 that is fixed to the skull. Therefore, when the deep intracranial electrode 100 is under a pulling force, the fixing nut 200 may avoid the nonelastic sleeve 70 from moving, thereby avoiding the deep intracranial electrode 100 from being pulled out.

Furthermore, a part of the conducting wires 10 contained within the nonelastic sleeve 70 is longer than the nonelastic sleeve 70. While the deep intracranial electrode 100 is under a pulling force, the nonelastic sleeve 70 bears the tension, and the conducting wires 10 inside the nonelastic sleeve 70 may still keep a loose state all the time and avoid being damaged by the tension.

Furthermore, the nonelastic sleeve 70 is made of a transparent material, which is convenient for a user to check the status of the conducting wires 10 contained inside the nonelastic sleeve 70. Furthermore, the nonelastic sleeve 70 may also adopt a non-magnetic material, thereby avoiding interference of radio-frequency electromagnetic wave in the process of transmitting electrophysiological signals.

Furthermore, one end of the nonelastic sleeve 70 sheathes around the connector 30, the other end sheathing around the fixing nut 200. In addition, the nonelastic sleeve 70 may fasten to the connector 30 and the fixing nut 200 via a hoop. Therefore, the nonelastic sleeve 70 is merely connected to the connector 30 and the fixing nut 200 when necessary, and may be replaced if damaged.

It's worth mentioning that the deep intracranial electrode 100 in the present embodiment further includes a connecting member (not shown), one end of the connecting member is connected to the electrode contact 20, the other end is connected to the connector 30. Furthermore, a part of the connecting member between the electrode contact 20 and the connector 30 is shorter than a part of the conducting wires 10 between the electrode contact 20 and the connector 30. The connecting member between the electrode contact 20 and the connector 30 is shorter than the part of the conducting wires 10 between the electrode contact 20 and the connector 30. When the deep intracranial electrode 100 is under a pulling force, the connecting member bears the tension, improving tensile strength of the deep intracranial electrode 100 and avoiding the deep intracranial electrode 100 from broken accidentally in the process of detection. In the present embodiment, the material of the connecting member is a tensile material such as fiberglass, which is easy to obtain and will not interfere radio-frequency magnetic field of the magnetic resonance equipment. Surely, in alternative embodiments, the connecting member may adopt alternative materials with greater tensile strength.

Furthermore, the deep intracranial electrode 100 further includes a flexible insulation sleeve 80 sheathing around the conducting wires 10, one end of the flexible insulation sleeve 80 connected to the electrode contacts 20, the other end connected to the casing. It is understood that the flexible insulation tube 80 integrates multiple conducting wires into a bundle, thus making the conducting wires 10 arranged more orderly. It may also avoid the conducting wires 10 from exposure, improve the safety performance and service life of the deep intracranial electrode 100, and better the data transmission stability. In addition, the electrode contacts 20 in the present embodiment are of an annular structure. The electrode contacts 20 sheath around the flexible insulating tube 80, which increases contact area between the electrode contacts 20 and the patient's deep brain tissue.

Figure 11:
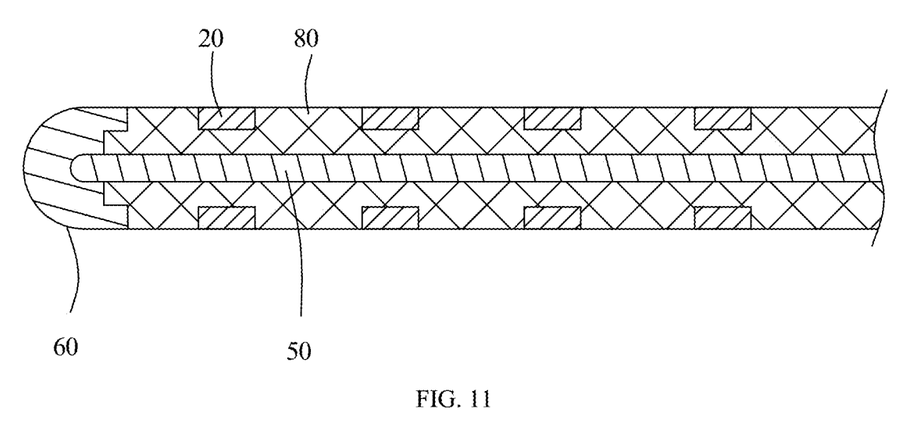
FIG. 11 is a schematic view of a partial structure of the deep intracranial electrode in FIG. 1.

As shown in FIG. 11, the deep intracranial electrode 100 further includes a rigid support rod with a certain stiffness. The rigid support rod 50 passes through the flexible insulation sleeve 80, such that the flexible insulation sleeve 80 is straight, therefore, one end of the deep intracranial electrode 100 connected to the electrode contact 3 may be implanted into the skull the patient conveniently. Furthermore, the rigid support rod 50 in the present embodiment is made of a shape memory material, such as a shape memory alloy material, or a shape memory ceramic material. Therefore, the rigid support rod 50 may recover to its original shape after being bent under external forces, avoiding scraping the deep intracranial electrode 100 completely for the bending of the rigid support rod 50.

Furthermore, the deep intracranial electrode 100 further includes an end electrode 60. The end electrode 60 is connected to the rigid support rod 50 and is electrically connected to the connector 30 via the conducting wires 10. The end electrode 60 may collect electrophysiological signals of a patient's deep brain tissue. Furthermore, the end electrode 60 also provides therein with an electromagnetic induction element for marking the location of the end electrode 60, such that location information of the end electrode 60 may be fed back to external equipment.

Disclosures above only describe preferable embodiments of the present application, and should not be deemed as limiting the protection scope of the present application. Equivalent modifications based on the appended claims should also fall within the protection scope of the present application.

What is claimed is:

1. A deep intracranial electrode adapted to be used with a magnetic resonance equipment, comprising,
    conducting wires, wherein an entire longitudinal length of the conducting wires is a resonant length having a peak heating value when the conducting wires absorb a radio-frequency magnetic field wave generated by the magnetic resonance equipment;

electrode contacts connected to a distal end of the corresponding conducting wires and configured to contact a brain tissue to collect electrophysiological signals;

a connector connected to proximal ends of the conducting wires;

a shield sleeve disposed around the conducting wires and configured to shield from the radio-frequency magnetic field generated by the magnetic resonance equipment and lower the peak heating value of the conducting wires; and a non-elastic sleeve disposed around the conducting wires and the shield sleeve, wherein one end of the non-elastic sleeve is capable of being connected to the connector and the other end is connected to a fixing nut which is adapted to be fixed to a skull to prevent the non-elastic sleeve from moving; and wherein an equivalent length of the conducting wires inside the radio-frequency magnetic field generated by the magnetic resonant equipment equals to a sum of the length of the shield sleeve and a length of the conducting wires outside the shield sleeve, and wherein the equivalent length is shorter than the resonant length of the conducting wires and the corresponding heating value of the equivalent length is lower than the corresponding peak heating value of the resonant length of the conducting wires to lower the heating of the conducting wires during a magnetic resonance imaging.

2. The deep intracranial electrode of claim 1, wherein parts of the conducting wires within the non-elastic sleeve is longer than the non-elastic sleeve.

3. The deep intracranial electrode of claim 1, wherein the non-elastic sleeve is made of a transparent material.

4. The deep intracranial electrode of claim 1, wherein one of the non-elastic sleeve sheathes around the connector, the other end sheathing around the fixing nut.

5. The deep intracranial electrode of claim 1, wherein the non-elastic sleeve is made of a non-magnetic material.

6. The deep intracranial electrode of claim 1, wherein the deep intracranial electrode further includes a connecting member, one end of the connecting member is connected to the electrode contacts, the other end is connected to the connector; and the connecting member between the electrode contacts and the connector is shorter than the conducting wires between the electrode contact and the connector.

7. The deep intracranial electrode of claim 6, wherein the connecting member is made of a tensile material.

8. The deep intracranial electrode of claim 1, wherein the shield sleeve is shorter than the conducting wires, and the conducting wires is capable of being folded inside the shield sleeve.

9. The deep intracranial electrode of claim 1, wherein the shield sleeve being capable of moving axially along and relative to the conducting wires so as to change a length of a part of the shield sleeve sheathing around the conducting wires.

10. The deep intracranial electrode of claim 6, wherein the connector comprises a casing and a plurality of pins arranged inside the casing, the casing connecting to the connecting member; and each of the conducting wires is connected to a corresponding one of the plurality of pins and a corresponding one of the electrode contacts.

11. The deep intracranial electrode of claim 1, wherein the conducting wires and the electrode contacts are both made of non-magnetic materials.

12. The deep intracranial electrode of claim 1, wherein the deep intracranial electrode further includes a flexible insulation sleeve sheathing around the conducting wires, one end of the flexible insulation sleeve is connected to the electrode contact, the other end is connected to the connector; the deep intracranial electrode further includes a rigid support rod, the rigid support rod passes through the flexible insulation sleeve and is arranged at one end of the flexible insulation sleeve connected to the electrode contact.

13. The deep intracranial electrode of claim 12, wherein the rigid support rod is made of a shape memory material.

14. The deep intracranial electrode of claim 12, wherein the deep intracranial electrode further includes an end electrode, the end electrode is connected to one end of the rigid support rod away from the connecting member and electrically connected to the connector via a corresponding one of the conducting wires.

15. The deep intracranial electrode of claim 1, wherein each of the electrode contacts is of an annular shape.

* * * * *